(12) United States Patent
Rodgers et al.

(10) Patent No.: US 8,386,044 B2
(45) Date of Patent: Feb. 26, 2013

(54) COMPLEX CONNECTOR IN COMPONENT FOOTPRINT OF IMPLANTABLE MEDICAL DEVICE

(75) Inventors: Angela Rodgers, Minneapolis, MN (US); Andrew J. Ries, Lino Lakes, MN (US); Kurt J. Casby, Grant, MN (US); John D. Norton, New Brighton, MN (US); Mark D. Breyen, Plymouth, MN (US); Dan D. Erklouts, Brooklyn Center, MN (US); Brian J. Ross, Maple Grove, MN (US); Timothy T. Bomstad, Inver Grove Heights, MN (US); Wayne L. Appleseth, Lino Lakes, MN (US); Michael E. Clarke, St. Michael, MN (US); Jeffrey L. Kehn, Chaska, MN (US); Scott J. Robinson, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 1259 days.

(21) Appl. No.: 11/290,282

(22) Filed: Nov. 30, 2005

(65) Prior Publication Data

US 2006/0172611 A1 Aug. 3, 2006

Related U.S. Application Data

(62) Division of application No. 10/266,651, filed on Oct. 7, 2002, now Pat. No. 8,249,710.

(51) Int. Cl.
*A61N 1/00* (2006.01)
(52) U.S. Cl. ............................................. 607/36; 607/37
(58) Field of Classification Search ................. 607/5, 36, 607/37
See application file for complete search history.

(56) References Cited

U.S. PATENT DOCUMENTS

| | | | |
|---|---|---|---|
| 4,571,662 A | 2/1986 | Conquest et al. | |
| 5,522,851 A | 6/1996 | Fayram | |
| 5,801,917 A | 9/1998 | Elias | |
| 5,814,082 A | 9/1998 | Fayram et al. | |
| 5,926,357 A | 7/1999 | Elias et al. | |
| 5,954,751 A | 9/1999 | Chen et al. | |
| 6,009,348 A | 12/1999 | Rorvick et al. | |
| 6,014,586 A | 1/2000 | Weinberg et al. | |
| 6,026,325 A | 2/2000 | Weinberg et al. | |
| 6,032,075 A | 2/2000 | Pignato et al. | |
| 6,040,082 A | 3/2000 | Haas et al. | |
| 6,099,600 A | 8/2000 | Yan et al. | |
| 6,102,734 A * | 8/2000 | Kuo ............................ | 439/545 |
| 6,110,233 A | 8/2000 | O'Phelan et al. | |
| 6,118,652 A | 9/2000 | Casby et al. | |
| 6,141,205 A | 10/2000 | Nutzman et al. | |
| 6,157,531 A | 12/2000 | Breyen et al. | |
| 6,191,931 B1 | 2/2001 | Paspa et al. | |
| 6,212,063 B1 | 4/2001 | Johnson et al. | |

(Continued)

FOREIGN PATENT DOCUMENTS

| | | |
|---|---|---|
| EP | 1053763 A2 | 11/2000 |
| WO | WO03090862 A1 | 6/2003 |

OTHER PUBLICATIONS

Surface Mount PCB Test Points, Precision Interconnect, Feb. 18, 1999 (http://web.archive.org/web/*/http://www.oxley.co.uk/interconnect/smox.html;).

(Continued)

*Primary Examiner* — Scott M Getzow
(74) *Attorney, Agent, or Firm* — Carol F. Barry

(57) ABSTRACT

A complex connector and component within an implantable medical device in which the complex connector is positioned within the spacing footprint of the component to optimize packaging within the device.

9 Claims, 9 Drawing Sheets

U.S. PATENT DOCUMENTS

| | | | |
|---|---|---|---|
| 6,243,605 | B1 | 6/2001 | Youker et al. |
| 6,251,124 | B1 | 6/2001 | Youker et al. |
| 6,321,114 | B1 | 11/2001 | Nutzman et al. |
| 6,385,490 | B1 | 5/2002 | O'Phelan et al. |
| 6,388,866 | B1 | 5/2002 | Rorvick et al. |
| 6,402,793 | B1 | 6/2002 | Miltich et al. |
| 6,426,864 | B1 | 7/2002 | O'Phelan et al. |
| 6,445,948 | B1 | 9/2002 | Somdahl et al. |
| 6,459,566 | B1 | 10/2002 | Casby et al. |
| 6,514,276 | B2 | 2/2003 | Munshi |
| 6,699,265 | B1 | 3/2004 | O'Phelan et al. |
| 6,885,887 | B2 | 4/2005 | O'Phelan et al. |
| 2001/0011183 | A1 | 8/2001 | Munshi |
| 2002/0108221 | A1 | 8/2002 | Miltich et al. |
| 2002/0133209 | A1 | 9/2002 | O'Phelan et al. |
| 2003/0204216 | A1* | 10/2003 | Ries et al. .................. 607/36 |

OTHER PUBLICATIONS

Tips for Designing PCBs, ExpressPCB, Feb. 21, 1999 (http://web.archive.org/web/*/http://www.expresspcb.com/ExpressPCBHtm/Tips.htm).

Topower 420, 470, and 520 watt ATX power supplies, Dansdata, Aug. 9, 2001 (http://web.archive.org/web/*/http://www.dansdata.com/top420p4.htm; http://www.dansdata.com/top420p4.htm).

* cited by examiner

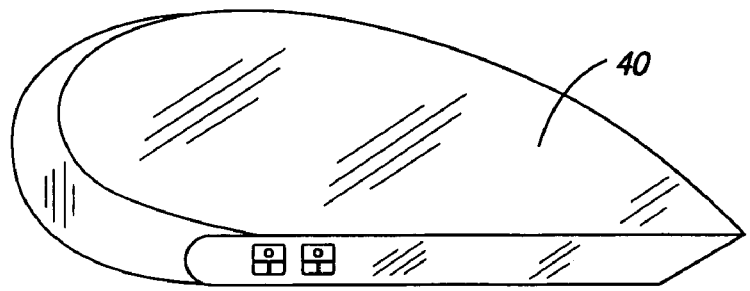
FIG. 3
(PRIOR ART)
FIG. 4
(PRIOR ART)
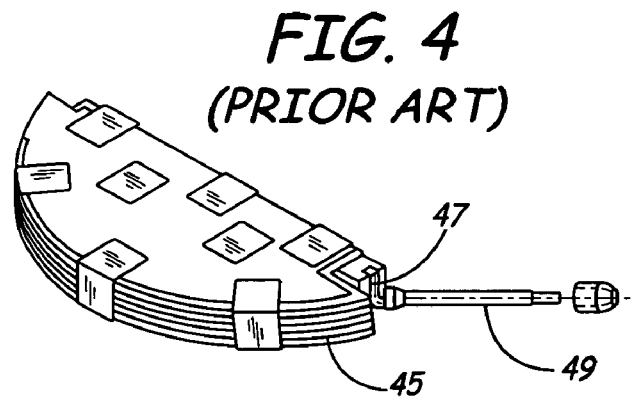
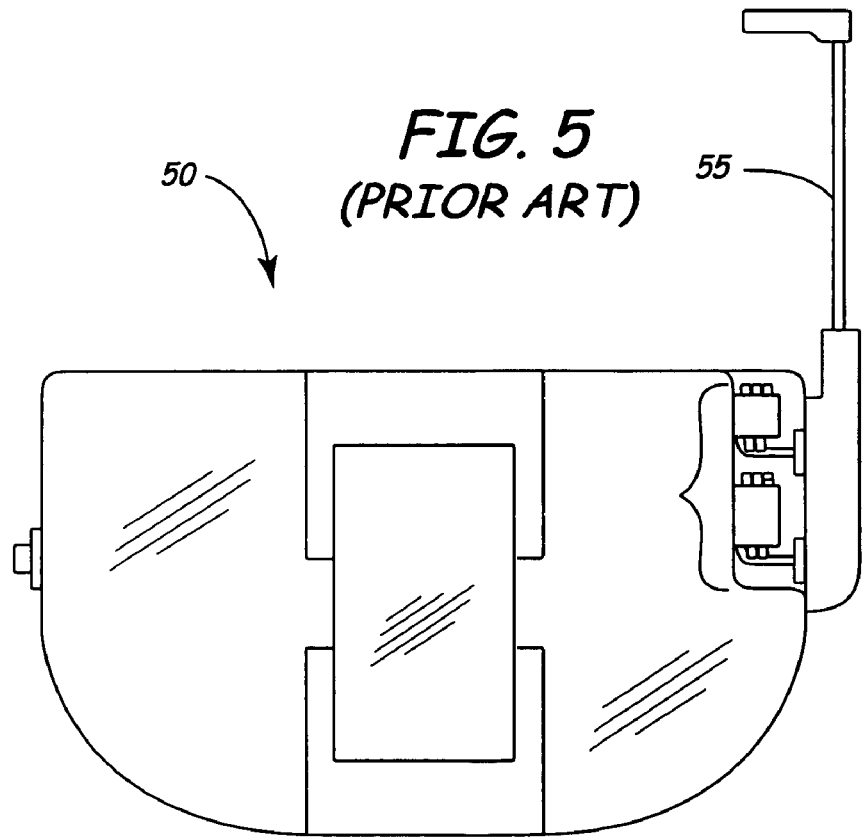
FIG. 5
(PRIOR ART)

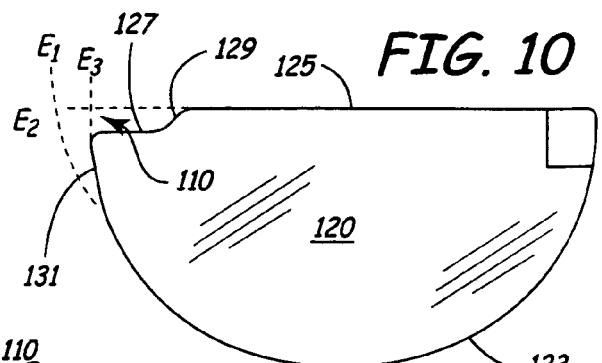
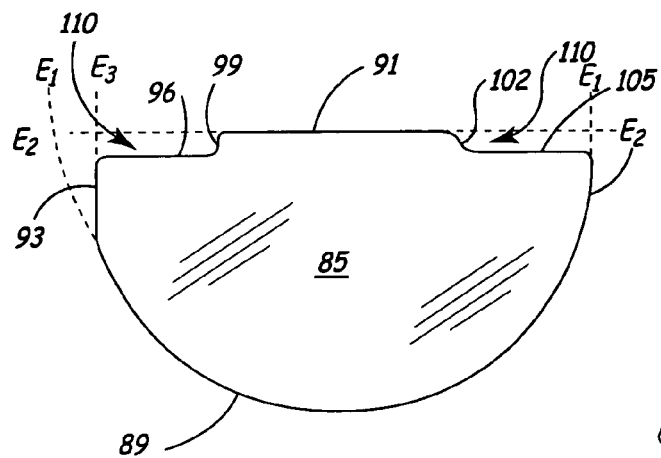
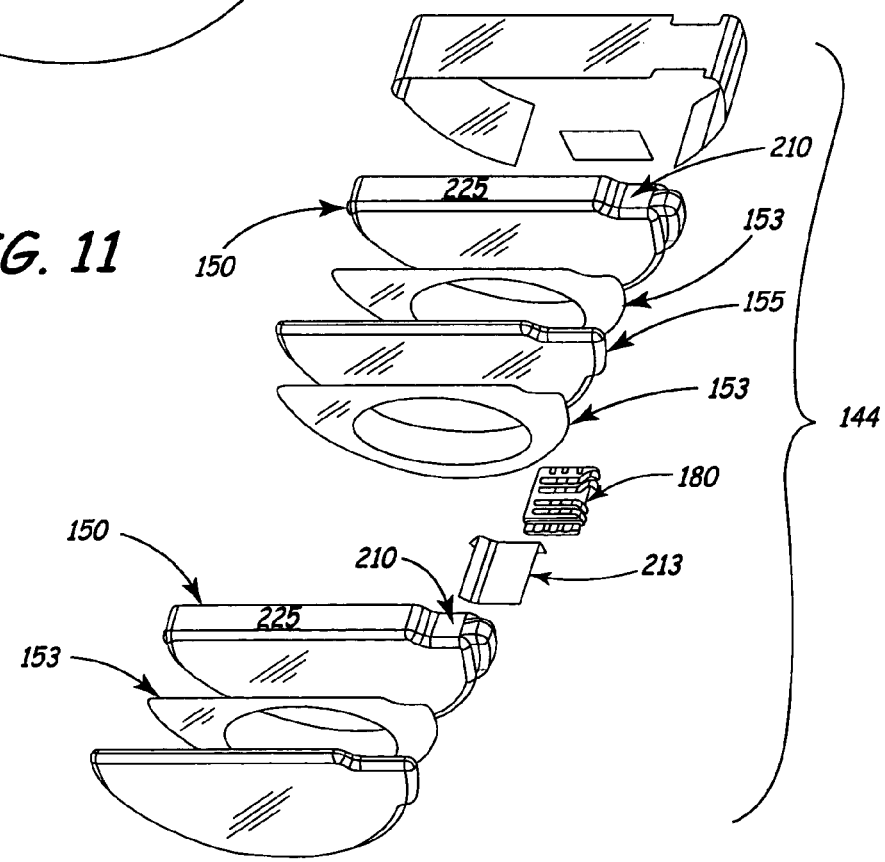

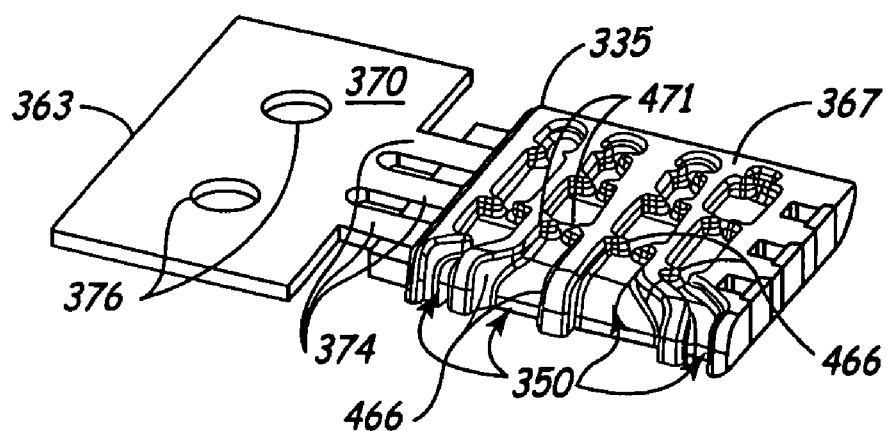
FIG. 15
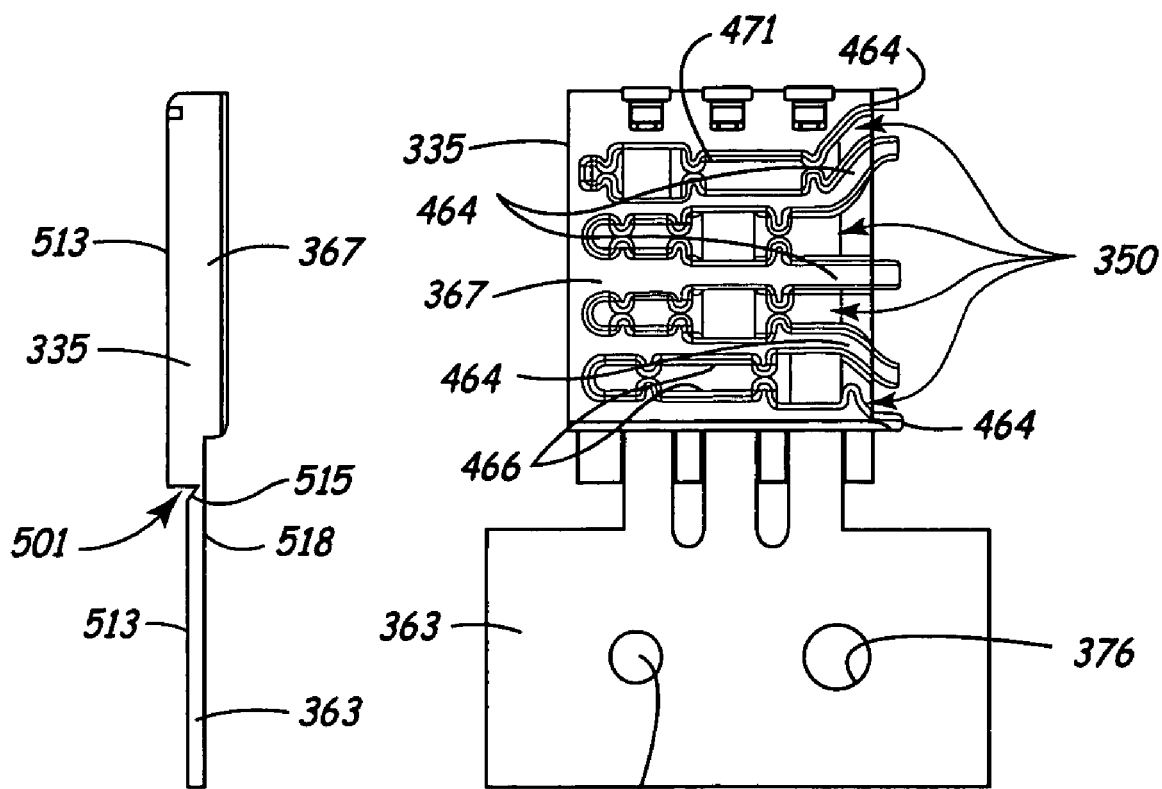
FIG. 17
FIG. 16

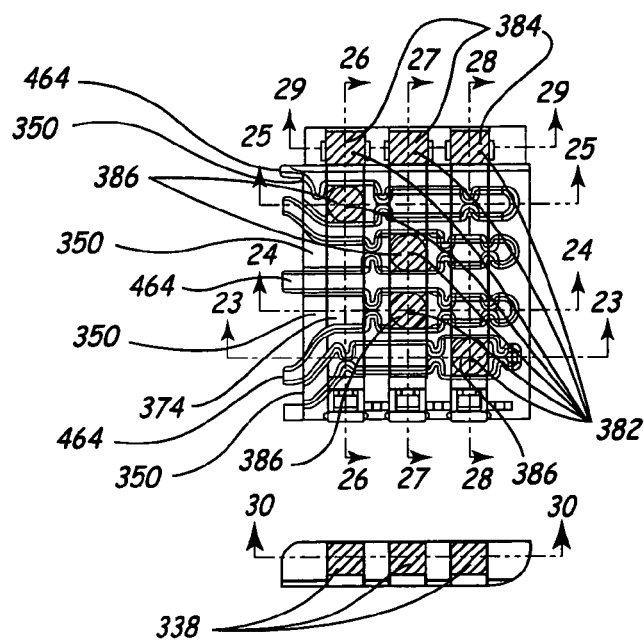
FIG. 18
FIG. 19
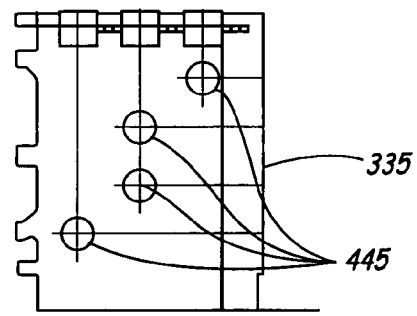
FIG. 20
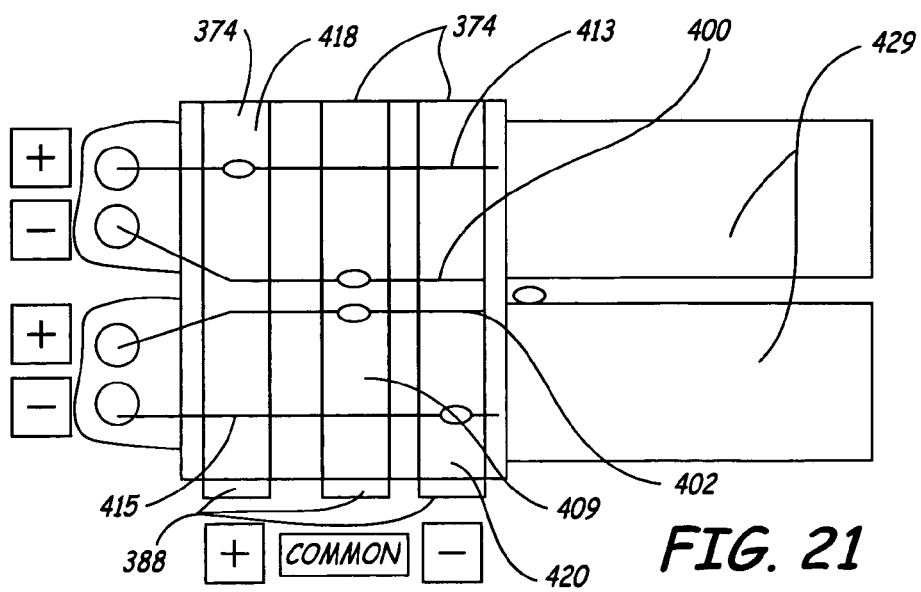
FIG. 21

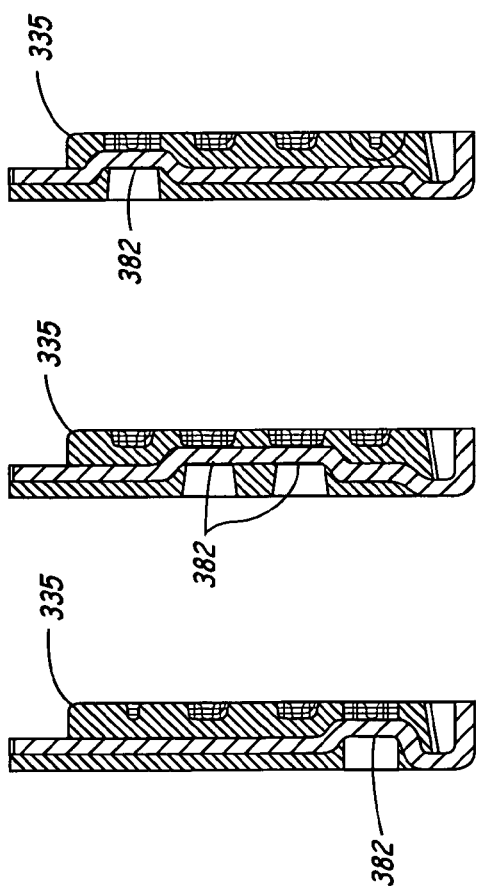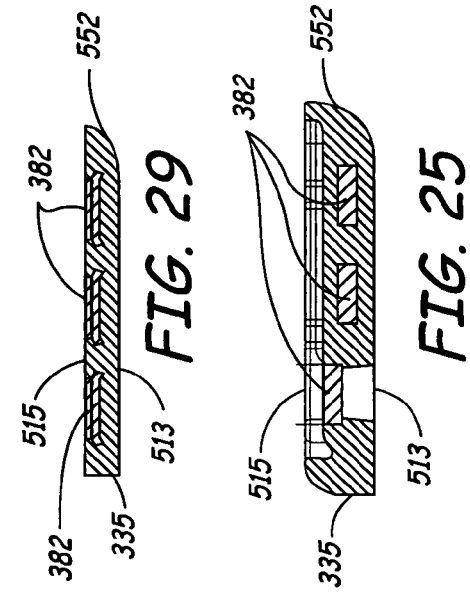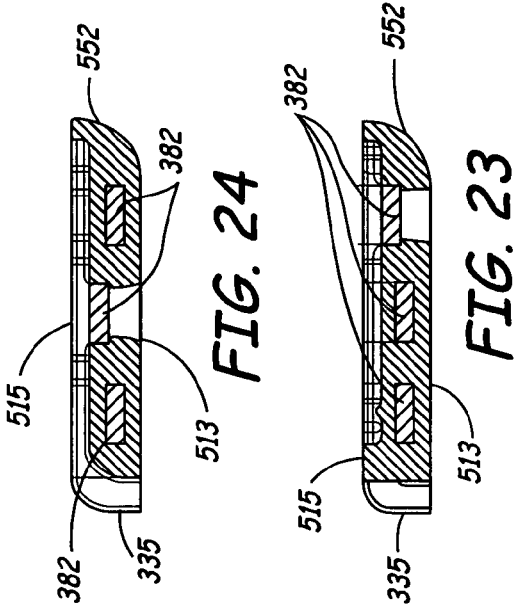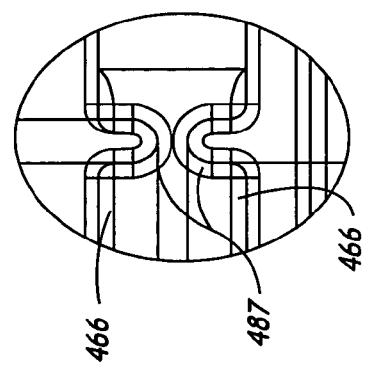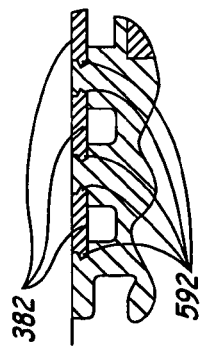

COMPLEX CONNECTOR IN COMPONENT FOOTPRINT OF IMPLANTABLE MEDICAL DEVICE

This application is a divisional of prior application Ser. No. 10/266,651, filed Oct. 27, 2002, now abandoned entitled "Complex Connector in Component Footprint of Implantable Medical Device."

FIELD OF THE INVENTION

An energy storage and delivery component for an implantable medical device having an imbedded electrical connector.

BACKGROUND OF THE INVENTION

Within the field of implantable medical devices, there exists a constant need to reduce the space and volume requirements of each device while increasing the capabilities of the same device. Considerable improvements in capability have occurred with developments in the power management and electronics assemblies in such devices. Further developments included shaping of components within the devices to permit improved outer shaping of the devices.

One class of internal components of such devices is an energy storing and delivery component, such as a battery or capacitor. Again, improvements in the design of this class of component have resulted in reduced space and volume requirements while maintaining capabilities. Yet this area has overlooked the use of certain improvements to achieve more efficient manufacturing and packaging attributes.

SUMMARY OF THE INVENTION

Applicants have identified methods and structure to permit the use of compound side shapes on the housings of energy storage and delivery devices which enable flush mounting of improved electrical connectors. In one embodiment, a method is taught for assembling an electrical connector with an energy storage and delivery component for use within an implanted medical device. The method comprises the steps of providing an energy storage and delivery component that is shaped to connect with an embedded complex electrical connector. The embedded electrical connector is sized to fit within a space formed within a notched zone defined by linear extensions of two perimeter surfaces of the energy storage and delivery component. A metallic insert is stamped out of raw sheet stock and then metal plated with a conductive plating material. A resinous connector portion is injection or cast molded with the metallic insert forming an integrated electrical connector for use in the implantable medical device, with said forming comprising creation of channel shaped wire-ways each sized to receive an un-insulated electrical wire connector from the energy storage and delivery device component. The electrical connector is then positioned into the notched zone on the energy storage and delivery device, and either an insulated or an un-insulated electrical wire then positioned into a wire-way.

In another embodiment, an implantable medical device having at least one capacitor for storing and delivering electrical energy on demand is provided. The at least one capacitor has a related connector for electrically connecting the capacitor with at least one other component within the device. The capacitor is shaped to connect with an embedded electrical connector which is sized to fit within a space formed within a zone defined by linear extensions of two perimeter surfaces of the capacitor.

In another embodiment, an implantable cardiac defibrillation device is provided which includes at least one flat capacitor for storing and delivering electrical energy on demand. The capacitor has at least a 30 Joule capacity; and the device has a volume of less than about 36 cubic centimeters and a thickness of less than about 15 millimeters, although other configurations are also disclosed.

The capacitor also has a related connector for electrically connecting the capacitor with at least one other component within the device. The capacitor is shaped to connect with the embedded electrical connector that is sized to fit within a space formed within a zone defined by linear extensions of two perimeter surfaces of the capacitor.

In yet another embodiment, an implantable medical device electrical connector is provided for connecting at least one energy storage and delivery component to at least one other component within the device. The connector comprises a stamped metallic portion for providing electrical connection between electrical connectors of an energy storage and delivery component and another component within the implantable medical device. The connector also has an injection molded connector portion formed in contact with the stamped metallic portion to provide a plurality of wire pathways shaped to receive electrical connectors from at least one energy storage and delivery component. The wire pathways also guide the energy storage and delivery component electrical connectors into selective electrical contact with conductive portions of the stamped metallic portion.

BRIEF DESCRIPTION OF THE DRAWINGS

FIG. 3 is a perspective view of a prior art implantable medical device component.

FIG. 4 is a perspective view of a prior art implantable medical device component internal configuration.

FIG. 5 is a side elevation partial cutaway view of a prior art component with protruding connection structure.

FIG. 9 is plan view of a cover for a component according to one embodiment of the invention.

FIG. 10 is a plan view of a cover of a component according to one embodiment of the invention.

FIG. 11 is an exploded perspective view of capacitor assembly according to one embodiment of the invention.

FIG. 15 is a perspective view of one embodiment of the connector according to the invention.

FIG. 16 is a top plan view of the connector of FIG. 15.

FIG. 17 is a side elevation view of the connector embodiment of FIG. 16.

FIG. 18 is a top plan view of an assembled connector embodiment.

FIG. 19 is side elevation view of the connector of FIG. 18.

FIG. 20 is bottom plan view of the connector of FIG. 18.

FIG. 21 is a top plan schematic view of the polarity scheme of one embodiment of a connector according to the invention.

FIG. 22 is an enlarged schematic view of a portion of the connector.

FIG. 23 is a section view taken along lines 23-23 of FIG. 18.

FIG. 24 is a section view taken along lines 24-24 of FIG. 18.

FIG. 25 is a section view taken along lines 25-25 of FIG. 18.

FIG. 26 is a section view taken along lines 26-26 of FIG. 18.

FIG. 27 is a section view taken along lines 27-27 of FIG. 18.

FIG. 28 is a section view taken along lines 28-28 of FIG. 18.

FIG. 29 is a section view taken along lines 29-29 of FIG. 18.

FIG. 30 is a section view taken along lines 30-30 of FIG. 19.

DETAIL DESCRIPTION OF THE INVENTION

Various techniques have been attempted and utilized to reduce the volume and improve the shape of implantable medical devices. In particular, those devices requiring discharge of high energy shocks such as implantable cardioverters or defibrillators require considerable efficiencies in order to maintain the overall device weight and size dimensions within commercial and medical tolerances. One area which has been overlooked as a source of improved packaging is that of reducing the margin area around sub-assemblies or components within such implantable medical devices. Rather it is quite common to have sizable percentages of dead space or non-useful volume within component housings and around the components themselves. Applicants have recognized this packaging problem and have identified several ways of reducing this lost volume while simultaneously decreasing the cost of assembling devices which achieve these benefits. Applicants are able to efficiently design and assemble energy storage and delivery components which are shaped to receive an embedded electrical connector placed within a zone defined by linear extensions of two perimeter or housing side surfaces of the energy storage and delivery device.

Figure 1:
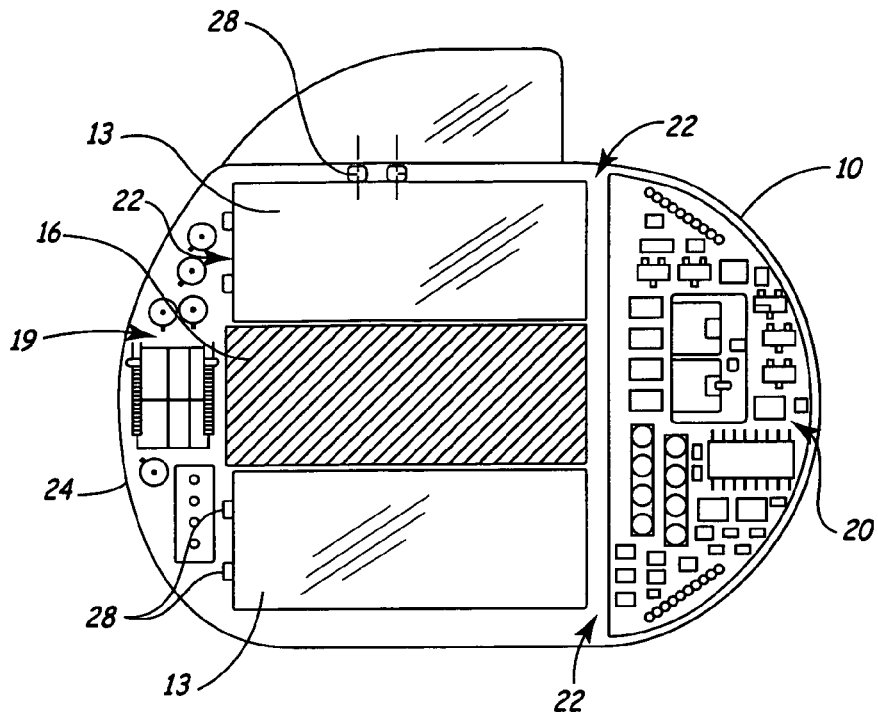
FIG. 1 is a plan view of a prior art implantable medical device.
Figure 2:
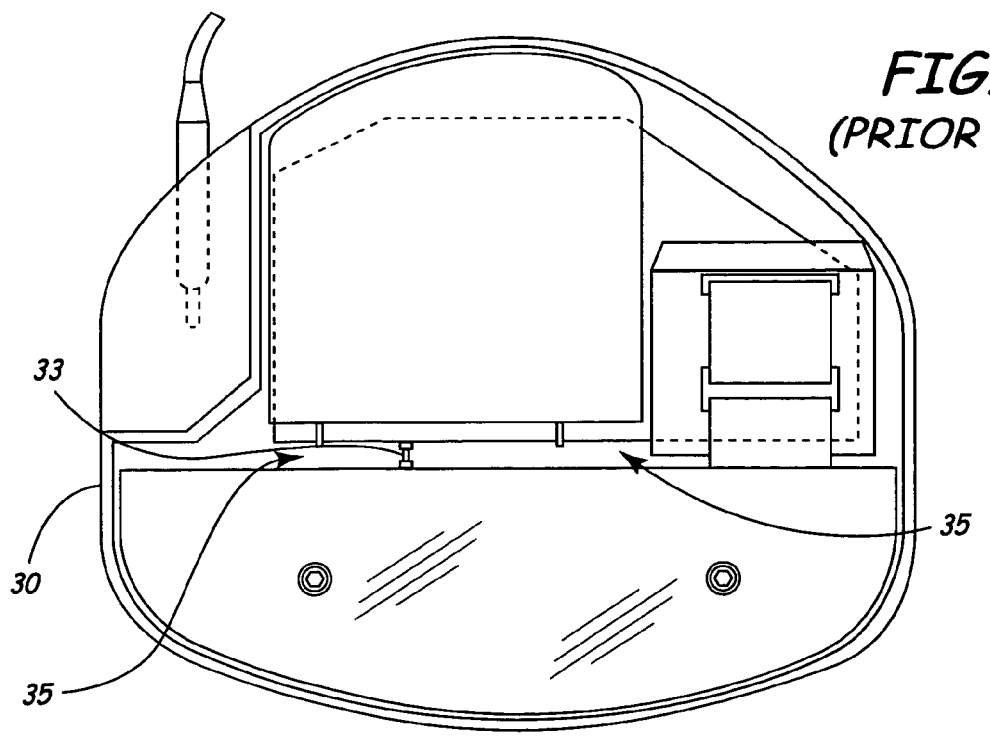
FIG. 2 is a plan view of a prior art implantable medical device.

Examples in the prior art demonstrate part of the need for these innovations. FIG. 1 is a plan view of an implantable cardioverter 10 which includes capacitors 13, a battery 16, and electronics assemblies 19, 20. As shown, for example at arrows 22, a considerable percentage of the volume within the device housing 24 is not used, or is partially used for electrical connection structure 28 protruding from the outer perimeter footprint of components. FIG. 2 is a plan view of an implantable cardiac defibrillator 30. Again, as shown by protruding electrical connector 33, the result of such protrusions or extensions beyond the perimeter footprint of components creates considerable unusable space shown by arrows 35. This is partly due to the inability of device manufacturers to make components in an integrated manner and with various shapes and sizes of components to accommodate and fit closely around protruding electrical connections.

Figures 6, 7, 8:
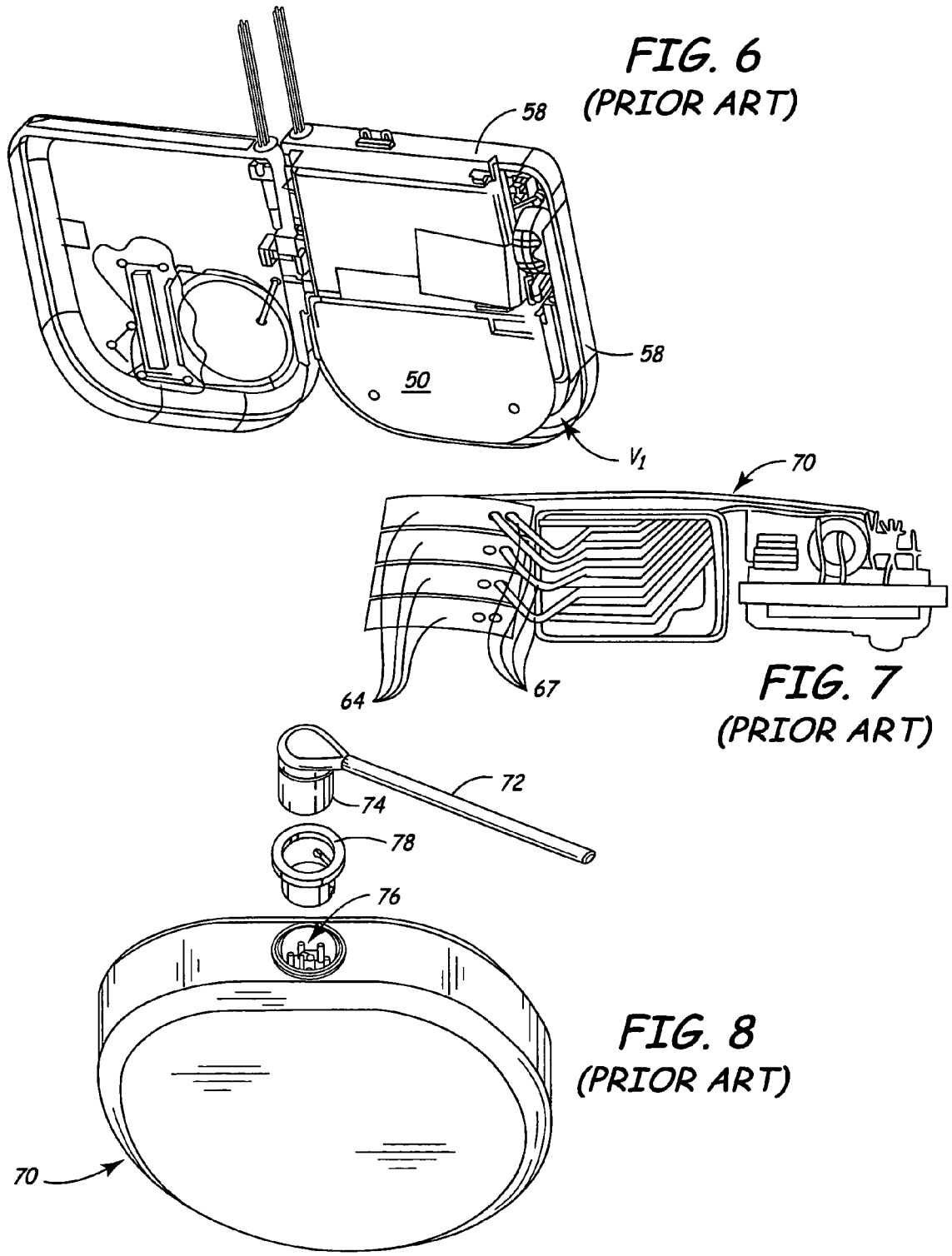
FIG. 6 is an elevation view of a prior art implantable medical device showing substantial margin area between a component and the housing side wall due to protruding connection structure.
FIG. 7 is a top view of a prior art connection scheme between a plurality of capacitors and another component in an implantable medical device.
FIG. 8 is an exploded elevation view of an external stimulation lead connection system for an implantable pulse generator.

It is recognized that known energy storing and delivery components for implantable medical devices, particularly capacitors, have a limited array of shapes. These include cylindrical, flat, semi-circle or rounded semi-rectangle. Other shapes are shown for example in U.S. Pat. No. 6,426,864, which includes that shape as depicted in capacitor 40 in FIG. 3. FIG. 4 discloses a capacitor 45 internal configuration as shown in U.S. Pat. No. 6,191,931. That figure also shows a feed-through wire 47 attached to anode tabs and designed for extending through and beyond a capacitor outer housing using a rigid plastic-encased sleeve 49. FIGS. 5 and 6 illustrate an energy storage and delivery component 50, which in this example is a capacitor, with protruding electrical connector 55. FIG. 6 shows the effect of a protruding electrical connector structure requiring inefficient use of substantial side volume $V_1$ between the component 50 and the device housing wall 58.

It is clear that there are undesirable packaging results of electrical connector structure which protrude beyond a component periphery or normal footprint within an implantable medical device. However, there are further negative effects (including, for example, electrical shorting, reliability, and liability exposure) which occur when attempts are made to use electrical connections that are loosely configured wires or not properly insulated or protected wires. One example of this is shown in FIG. 7 in which capacitors 64 are connected via loose wire connections 67 to an electrical assembly within an implantable cardiac defibrillator (ICD) 70. Electrical connections of this type are often hand manufactured by one or more technicians, rather than by an automated process operator (i.e., machine). This adds cost and may inject loss of reliability into the manufacturing process. FIG. 8 shows an external connection for a pulse generator 70, having a headerless design, aligned with the terminal end portion of a stimulating lead 72. The lead 72 has a connector 74 attached to the terminal end, wherein the connector 74 is adapted for connection with the feed-through assembly 76 of the pulse generator 70. An elastomeric boot 78 is sealingly engaged to the lead 72, whereby the boot may be slid over the lead to the terminal end of the lead, to thereby cover the connector 74. The invention of FIG. 8 relates to a connection of a stimulating lead for stimulating tissue to the external portion of a stimulation device. The figure not does relate to the connections or packaging between components within an implantable medical device.

What is needed to overcome these packaging concerns is an embedded connector block for use with an implantable medical device component, including, for example, an energy storage and delivery component, which integrates into a component footprint rather than adding to the footprint. FIGS. 9-32 show embodiments of devices, components, assemblies, sub-assemblies and connectors which achieve this goal. FIG. 9 is a plan view of a cover or housing 85 for a representative component, which in this embodiment is a capacitor. The housing has a plurality of outer peripheral surfaces 89, 91, 93, 96, 99, 102 and 105. As compared with known capacitor covers/housings, housing 85 has at least one additional surface in plan view. Actually, as compared to either a rectangular or semi-circular housing (or other energy storage and delivery device sized for placement therein) the housing shown in FIG. 9 discloses a plurality of notched zones 110 formed within an area defined by linear extensions (shown by dashed lines $E_1$ and $E_2$) of perimeter surfaces of the housing 85 (or energy storage and delivery component). An even smaller zone may be formed using linear extension $E_3$, if desired. Each notched zone 110 is sized to receive a complex electrical connector (shown and described later herein) which is designed for that zone, and said connector electrically connects at least one energy storage and delivery component to other components or assemblies within an implantable medical device. Other surfaces may be shaped to receive other complex connectors as well within similarly created zones which also remain within the conventional shape or footprint of the component. The creation of these zones virtually eliminates the protrusions and other problems shown in the prior art devices, including all of those shown in FIGS. 1-8, and enables improved packaging through closer flush-mounting of components and efficient use of such novel complex connectors as shown and described herein.

FIG. 10 is a plan view of another embodiment of a cover or housing 120 for a capacitor, such as a flat capacitor, which is nominally shaped as a curved semi-circle having surfaces 123, 125. Notched zone 110 is formed by addition of surfaces 127, 129, and, optionally, surface 131. The use of a housing is to hold a capacitor assembly as shown in FIG. 11, which is an exploded view of capacitor assembly 144. As shown, capacitor assembly 144 comprises at least one capacitor 150 (in this embodiment there are two illustrated) and peripheral material including for example positioning or adhesive material 153 and insulation material 155. In one embodiment, some or all of the peripheral material shown in FIG. 11 comprises an outer housing, and therefore the shape of the housing substantially matches that of any underlying capacitor(s) 150. In other embodiments, a housing may comprise other material surrounding at least part of at least one capacitor having outer surfaces forming at least one notched zone. The at least one notched zone is shaped to receive a complex electrical connector external of the housing but within the extended natural footprint (i.e., embedded) of the capacitor (energy storage and delivery device) if the capacitor did not have the peripherally located notched zones formed by additional surfaces.

FIG. 11 also shows an embodiment of a complex electrical connector 180 useful in combination with the formed notched zones described above. It is to be understood that a complex electrical connector means a structure that is more robust than a simple jumper wire or other single wire or single function electrical connection. In this embodiment, complex connector 180 is configured for attachment in zone 210 with a two sided adhesive material 213, although other attachment structure or method may be useful—provided that the connector is not significantly displaced and protruded out of its zone. Referring again to FIGS. 10 and 11, a goal of the notched zones is to enable placement of a certain inexpensive yet highly reliably manufactured electrical connector 180 in a notched zone so that the connector is not extending above surface 125 or 225. In addition, as shown below, the unique placement and configuration of connector 180 optimizes the close engagement, virtually flush mounting, of other components with capacitor 150. In these examples, due to the length of surfaces 125, 225 and the elimination of margin area by such flush mounting, there is considerable savings in volume for a device using this innovation.

Figure 12:
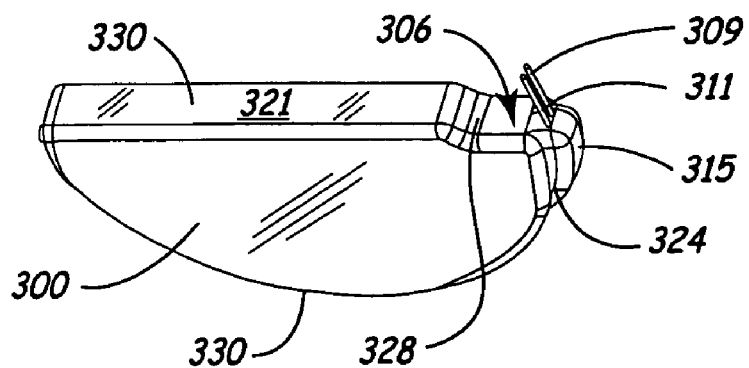
FIG. 12 is a perspective view of a capacitor having at least one notched zone according to one embodiment of the invention.

FIG. 12 is an elevation view of a single capacitor 300, having a novel notched zone 306 located immediately adjacent to the capacitor electrical leads 309, 311 which extend from epoxy or other structure 315. Zone 306 is bounded by the area within linear extensions of two perimeter surfaces 321, 324 of the capacitor and at least one third surface 328 of a perimeter portion 330 of the capacitor. Notched zone 306 is designed to receive an embedded complex electrical connector 335, shown in use with a pair of similarly shaped capacitors 300 in FIGS. 13 and 14.

Figure 13:
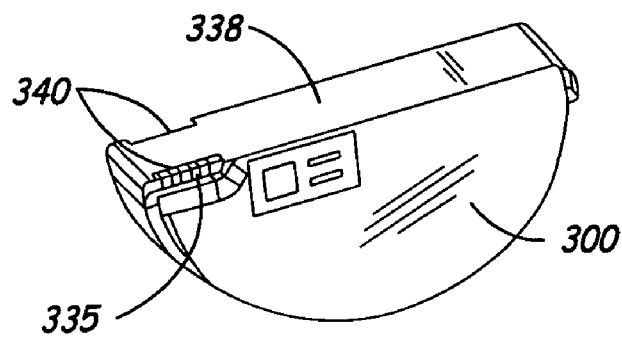
FIG. 13 is a perspective view of the capacitor embodiment of FIG. 12 shown with one embodiment of the connector.
Figure 14:
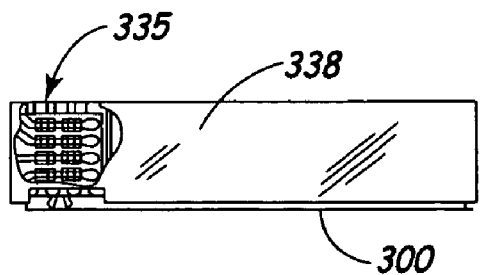
FIG. 14 is a top partial cutaway view of the embodiment of the invention shown in FIG. 13.

FIG. 13 also shows an insulator material 338 placed around the periphery of the combined capacitor hybrid assembly and connector. It is noted that the insulator material includes cutout segments 340 which permit access to conductive pads for either testing or further connection with other components, assemblies, or sub-assemblies within the device. FIG. 14 is a top view of the hybrid assembly with insulator 338 partially removed to see the wire connections and the relative layout and sizing of the connector 335.

FIGS. 15-17 show different views of a connector 335, which in this embodiment has four wire ways 350. It is understood that the invention may include connectors with a variety of wire way configurations. Connector 335 is preferably sized for integrated conformal fit within a notched zone of an associated component of an implantable medical device. In the following descriptions, one or more capacitors are selected as representative examples of such a component although other types of components may benefit from use of such a connector and are considered within the scope of this invention. Also, although various techniques may be used to manufacture connector 335, a preferred method allows dramatic cost savings other techniques. In one embodiment, electrical connector 335 is made with a stamped metallic portion 363 and an injection molded connector portion 367. It is also possible to use a cast molded resin or epoxy. Generally, these materials are also referred to herein as either thermoplastic or thermoset materials. The stamped metallic portion 363 provides electrical connection between electrical connectors of the one internal component or assembly and another component or assembly within the implantable medical device. The stamped metallic portion is preferably selected from a list of metals including nickel, titanium, copper, aluminum, tantalum, niobium, platinum, platinum family or alloys, stainless steel, palladium, rhodium, or other compatible conductive metals. In one preferred embodiment, stamped metallic portion 363 comprises a common lead frame 370 and a plurality of conductive stamping legs 374. In FIGS. 15-16, common lead frame 370 has keying structure 376 for positioning the piece during the assembly processes. The injection molded connector portion 367 is preferably formed in contact with stamped metallic portion 363 to provide a plurality of wire pathways 350 shaped to receive electrical connectors from at least one internal component or assembly and to guide the internal component or assembly electrical connectors into selective electrical contact with conductive pads 379 on the stamping legs 374. Accordingly, Applicants teach a method of assembling an electrical connector to an energy storage and delivery component for use within an implanted medical device. The method comprises the steps of providing an energy storage and delivery component that is shaped to connect with an embedded electrical connector that is sized to fit within a space formed within a notched zone defined by linear extensions of two perimeter surfaces of the energy storage and delivery component. First, a metallic insert is stamped out of raw sheet stock and then metal plated with a conductive plating material. Next, injection molding is used to form and attach a resinous connector portion with the metallic insert to create an integrated electrical connector. Preferably, the connector portion resin is selected from a list of resins including polyetheramide, polyurethane, nylon and other moldable, high temperature dimensionally stable, high dielectrically constant electrical insulators, having a high flashpoint threshold and a high flow rate. The forming step comprises creation of the channel shaped wire-ways (and other functional structure) with each wire way sized to receive an un-insulated electrical wire connector from the energy storage and delivery device component, i.e. capacitor hybrid assembly. The electrical connector is positioned in the notched zone on the energy storage and delivery device, and an un-insulated electrical wire is place into one or more of the wire-ways.

FIGS. 18-20 show top plan, side elevation and bottom plan views of a connector 335, with the plurality of conductive stamping legs 374 each having at least one conductive pad 382. In this embodiment, pads 382 are configured as exposed dedicated testing or shorting pads 384, resistance spot weld (RSW) pads 386 for connection of capacitor wires to connector 335, and Lazar Ribbon Bond (LRB) pads 388 for connection points between the associated capacitor hybrid assembly and another portion of the implantable medical device internals. By referring to FIG. 21, a preferred and optimized polarity scheme is shown in relation to the top view of connector 335 in FIG. 18. As shown, the connector wire ways 350 are arranged so that two wires 400, 402 connect to a common stamping leg 409 and each of the two additional wires 413, 415 are split among the positive and negative voltage stamping legs 418, 420. This facilitates converting four connection points from a two capacitor hybrid assembly 429 into a three connection point arrangement for connection with another portion of the implantable medical device at pads 388. Features 449 on the bottom surface of the connector 335 are configured with surfaces to permit improved holding during the molding operation. This facilitates obtaining a flash free surface on the RSW pads 386 as well as providing access to the bottom of pads 386 for opposed electrode resistance spot welding operations. It is understood that although RSW and LRB techniques are currently used to place certain conductive pads, the use of parallel gap welding (PGW), lazar welding, or other techniques may be used for these connections.

FIGS. 15, 16, 18, and 22 show each wire way 350 separated by a finger element 464 formed by wall portions 466, including tapered or stepped down portions 471. Finger elements 464 of the resinous material extend above the height of the wire when it is placed in each wire way 350 and thereby isolates each wire and prevents wire-to-wire contact within the connector. In preferred embodiments, the lengths of wire ways 350 are designed to receive wires which are cut to optimize automatic machine assembly and packaging within the wire ways. In one embodiment, each wire way wall portion 466 comprises a resilient restriction 485 formed of a pair of opposing wall protrusions 487 shaped to allow a centered press fit of a wire into the wire way and to then resiliently hold the wire in proper place. Again, this facilitates the automatic, efficient, and reliable assembly of the components and the device.

Additional features are added to connector 335. For example, FIG. 17 shows the stamped metallic portion having a breakaway groove 501 in a lower surface 513 between the common lead frame and the stamping legs. That portion of upper surface 515 that is opposite breakaway groove is flat, i.e. without a groove, to assist in the clean break of the material. Also, breakaway groove 501 comprises wall portions 518 shaped to allow reliable separation of the common lead frame from the stamping legs to eliminate any post-molding trim of the injection molded connector. Also, the wall portions 518 are arranged to direct the separation of the common lead frame from the stamping legs at a location inside an outer periphery of the connector to provide a flash free shutoff at the groove locations.

Connector 335 is manufactured so that conductive pads 382 are configured at different heights from a lower surface plan of the conductive stamping legs. This is shown in FIGS. 23-29, which correspond to the several sectional views of FIG. 18. The different heights are achieved in the stamping process and maintained with tooling in the molding process. The different elevations allow the connecting wires from the capacitor or other components to be routed over electrical pathways that the wires are not to be connected with without concern for shorting to those pathways. Yet another improvement is shown in FIG. 30, in which the conductive pads 382 may have one or more anchor tab structures 592 which extend into the conductive stamping legs and fix the location of the pads to facilitate automated assembly processes. Further reliability and innovation is achieved by use of a directional burr on the upper surface 515 of the metallic portion of the connector to ensure proper shutoffs during the injection molding processes.

Figure 31:
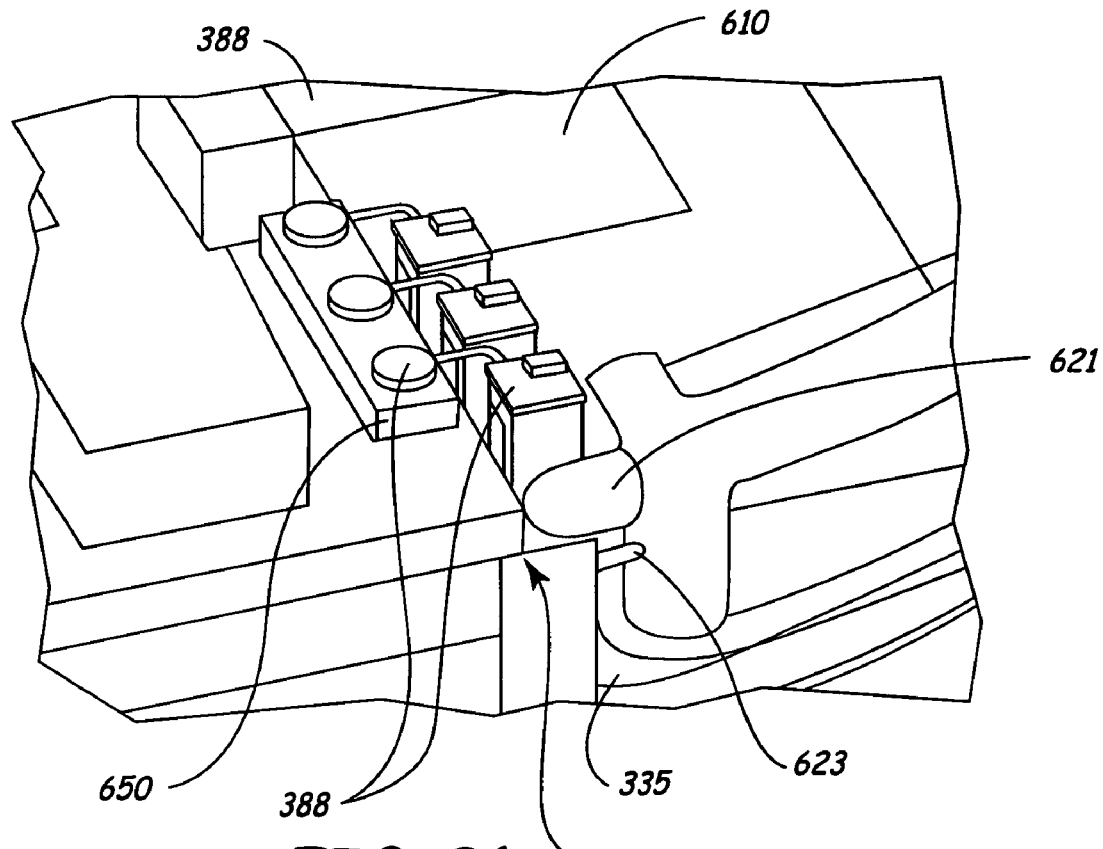
FIG. 31 is a perspective representation view of component packaging within an implantable medical device according to one of embodiment of the invention.

FIGS. 23-25 and 29 show connector lower surface 513 formed with a curved portion 552 leading up to upper surface 515, and shaped to conform to at least one additional perimeter surface of an associated component, whether it is an energy storage and delivery component, a capacitor, a battery, or another component or assembly. This and other features described herein enable advantageous use of an embedded electrical connector that is sized and shaped to fit within a space defined by linear extensions of two perimeter surfaces of a capacitor (or other component/assembly) and by at least one additional perimeter surface of the capacitor (component/assembly) which forms a notched area. This allows another component within the device to be positioned in abutting relation to the capacitor (component/assembly) with the connector integrated between the two components without creating any margin between the other component and the associated component. FIG. 31 illustrates this packaging configuration enabled by use of notched area or zone 610. In this zone is a connector 335 shown electrically connected with component electrical wires 621, 623 and with pads 388 connected to electrical leads of an abutting component 650. As shown at arrow 658, the packaging innovations of Applicants now permit placement of affected components in an implantable medical device in a relation which virtually eliminates the margin areas (which are common in known devices) around such components.

In addition to the considerable manufacturing efficiencies and cost savings which result from use of this invention, improved implantable medical devices are enabled. For example, in one embodiment there is provided at least one capacitor (or other energy storage and delivery component) for storing and delivering electrical energy on demand that has at least a 30 Joule capacity, a volume of less than about 36.5 cubic centimeters and a thickness of less than about 14 millimeters. In another embodiment, the invention includes at least one capacitor for storing and delivering electrical energy on demand which has at least a 30 Joule capacity, a volume of less than about 33 cubic centimeters and a thickness of less than about 13.5 millimeters. A further embodiment has at least one flat capacitor for storing and delivering electrical energy on demand, and the capacitor has at least a 30 Joule capacity. In this embodiment the device has a volume of less than about 36 cubic centimeters and a thickness of less than about 15 millimeters. In each of these embodiments, the capacitor has a related connector for electrically connecting the capacitor with at least one other component within the device. The capacitors are shaped to connect with an embedded electrical connector that is sized to fit within a space formed within a zone defined by linear extensions of two perimeter surfaces of the capacitor.

Another way of expressing this invention is an implantable medical device which has at least one internal component for energy storage and delivery of a defibrillation shock to a user. The internal component has a first energy storage and delivery capacity and a first volume, and the internal component is shaped to connect with an embedded electrical connector that is sized to fit within a space formed within a zone defined by linear extensions of two perimeter surfaces of the internal component. The first storage and delivery capacity is at least as great as any other known energy storage and delivery internal component less than about 36 Joules, and the first volume is less than the volume of any other identified energy storage and delivery internal component having the identical energy storage and delivery capacity.

Figure 32:
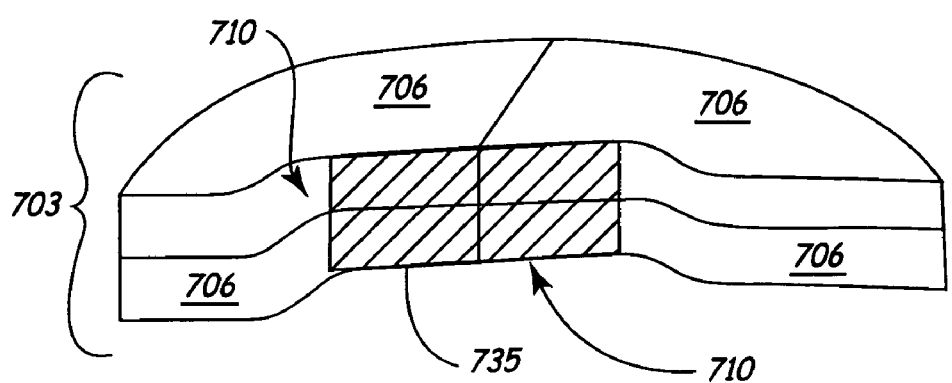
FIG. 32 is a perspective representation view of component packaging within an implantable medical device according to one of embodiment of the invention.

FIG. 32 shows a perspective view of another embodiment of an energy storage and delivery component hybrid assembly 703 comprising a plurality of components 706. In this embodiment a notched or other shape of a zone 710 is formed so as to permit shared central mounting of a complex electrical connector 735 (shown schematically) within the zone. This, again, exemplifies one of the various shapes and sizes of component which are possible for use within the scope of this invention.

Thus, embodiments of a connector block in a component footprint of an implantable medical device are disclosed. One skilled in the art will appreciate that the present invention can be practiced with embodiments other than those disclosed. For example, the connector block may be formed in an assembly of a plurality of sub-connector blocks. The disclosed embodiment are presented for purposes of illustration and not limitation, and the present invention is limited only by the claims that follow.

The invention claimed is:

1. An implantable cardiac medical device comprising:
at least one flat capacitor for storing and delivering electrical energy on demand, the capacitor having at least a 30 Joule capacity; the device having a volume of less than about 36 cubic centimeters and a thickness of less than about 15 millimeters; and
said capacitor has a related connector for electrically connecting the capacitor with at least one other component within the device;
an embedded complex electrical connector,
wherein the capacitor is shaped to connect with the embedded complex electrical connector that is sized to fit within a space formed within a notched zone defined by linear extensions of two perimeter surfaces of a housing of the capacitor.

2. The device of claim 1 in which the embedded electrical connector comprises a stamped metal piece and an injection molded thermoplastic or cast thermoset piece forming a connector with at least four wire-ways each shaped to receive and protect a bare metal wire connector from an associated capacitor.

3. The device of claim 1 in which the embedded electrical connector is sized to fit within the space formed within the zone so that a wall to wall component may be positioned adjacent to the capacitor without the connector creating any margin area between the capacitor and the battery.

4. The device of claim 2 in which the connector wire ways are arranged so that two wire ways connect to a common electrical connector on the stamped metal piece and each of the two additional wires are split among the positive and negative voltage electrical connectors on the stamped metal piece, and wherein each wire way is bounded by finger elements of the thermoplastic or thermoset material raised above the height of the wire in each wire way.

5. An implantable cardiac defibrillator medical device comprising:
at least one internal component for energy storage and delivery of a defibrillation shock to a user, said internal component having a housing of a first volume and providing a first energy storage and delivery capacity; and
an embedded electrical connector;
said internal component is shaped to connect with the embedded electrical connector, the embedded electrical connector being sized to fit within a space formed within a notched zone defined by linear extensions of two perimeter surfaces of the internal component; and
said first storage and delivery capacity being less than about 40 Joules.

6. The device of claim 5 in which the at least one internal component is a flat capacitor.

7. The device of claim 5 in which the embedded electrical connector comprises a stamped metal piece and an injection molded thermoplastic or cast thermoset piece forming a connector with at least one wire-way shaped to receive and protect a bare metal wire connector from an associated capacitor.

8. The device of claim 5 in which the embedded electrical connector is sized to fit within the space formed within the zone so that a wall to wall component may be positioned adjacent to the capacitor without the connector creating any margin area between the capacitor and the battery.

9. The device of claim 5 in which the at least one capacitor for storing and delivering electrical energy on demand has at least a 30 Joule capacity, and a volume of less than about 35 cubic centimeters.

* * * * *